(12) United States Patent
Kiyohara et al.

(10) Patent No.: US 9,700,538 B2
(45) Date of Patent: Jul. 11, 2017

(54) CARDIOVASCULAR DISEASE PRIMARY PREVENTION AGENT FOR PATIENTS HAVING HIGH BLOOD LEVELS OF HIGH-SENSITIVITY C-REACTIVE PROTEIN

(71) Applicants: MOCHIDA PHARMACEUTICAL CO., LTD., Tokyo (JP); KYUSHU UNIVERSITY, NATIONAL UNIVERSITY CORPORATION, Fukuoka-shi, Fukuoka (JP)

(72) Inventors: Yutaka Kiyohara, Fukuoka (JP); Toshiharu Ninomiya, Fukuoka (JP); Takashi Yano, Tokyo (JP)

(73) Assignees: MOCHIDA PHARMACEUTICAL CO., LTD., Tokyo (JP); KYUSHU UNIVERSITY, NATIONAL UNIVERSITY CORPORATION, Fukuoka-shi (JP)

( * ) Notice: Subject to any disclaimer, the term of this patent is extended or adjusted under 35 U.S.C. 154(b) by 0 days.

(21) Appl. No.: 14/400,777

(22) PCT Filed: May 14, 2013

(86) PCT No.: PCT/JP2013/063419
§ 371 (c)(1),
(2) Date: Nov. 12, 2014

(87) PCT Pub. No.: WO2013/172344
PCT Pub. Date: Nov. 21, 2013

(65) Prior Publication Data
US 2015/0141510 A1 May 21, 2015

(30) Foreign Application Priority Data
May 15, 2012 (JP) .................... 2012-111900

(51) Int. Cl.
*A61K 31/232* (2006.01)
*A61K 31/202* (2006.01)
*G01N 33/68* (2006.01)
*G01N 33/92* (2006.01)
*G01N 30/88* (2006.01)

(52) U.S. Cl.
CPC .......... *A61K 31/232* (2013.01); *A61K 31/202* (2013.01); *G01N 33/6893* (2013.01); *G01N 33/92* (2013.01); *G01N 2030/8813* (2013.01); *G01N 2333/4737* (2013.01); *G01N 2800/2871* (2013.01); *G01N 2800/32* (2013.01); *G01N 2800/324* (2013.01); *G01N 2800/325* (2013.01)

(58) Field of Classification Search
CPC .............. A61K 31/232; A61K 31/202; G01N 33/6893; G01N 33/92
See application file for complete search history.

(56) References Cited

U.S. PATENT DOCUMENTS 7,498,359 B2  3/2009  Yokoyama et al.
8,367,725 B2  2/2013  Yokoyama et al.

FOREIGN PATENT DOCUMENTS

JP    2007-39452 A    2/2007
JP    2007-238594 A   9/2007
WO    WO 2010/093634 A1  8/2010

OTHER PUBLICATIONS

Extended European Search Report issued Nov. 24, 2015, in European Patent Application No. 13790182.3.
Hirai et al., "Lower Eicosapentaenoic Acid and Higher Arachidonic Acid Levels in Sera of Young Adults in the Netherlands than in Japan," Environmental Health and Preventative Medicine (Jul. 2000), vol. 5, pp. 60-65.
Ridker et al., "Plasma Concentration of C-Reactive Protein and Risk of Developing Peripheral Vascular Disease," Circulation (1998), vol. 97, pp. 425-428.
English translation of International Preliminary Report on Patentability and Written Opinion issued Nov. 27, 2014, in PCT International Application No. PCT/JP2013/063419.
Arima et al., "High-Sensitivity C-Reactive Protein and Coronary Heart Disease in a General Population of Japanese: The Hisayama Study", Arteriosclerosis, Thrombosis, and Vascular Biology, Journal of the American Heart Association, 28, 2008, pp. 1385-1391.
Hayakawa et al., "Association of Plasma Omega-3 to Omega-6 Polyunsaturated Fatty Acid Ratio with Complexity of Coronary Artery Lesion", Internal Medicine, 51, 9, Apr. 29, 2012, pp. 1009-1014.
International Search Report, issued in PCT/JP2013/063419, dated Aug. 27, 2013.
Ninomiya et al., "Relationship between the Ration of Serum Eicosapentaenoic Acid to Arachidonic Acid and the Risk of Death: The Hisayama Study", The 75th Annual Scientific Meeting of the Japanese Circulation Society, Abstract and program, OJ-140, Aug. 3-4, 2011.
Satoh et al., "Purified Eicosapentaenoic Acid Reduces Small Dense LDL, Remnant Lipoprotein Particles, and C-Reactive Protein in Metabolic Syndrome", Diabetes Care, vol. 30, No. 1, Jan. 2007, pp. 144-146.

(Continued)

*Primary Examiner* — Sahar Javanmard
(74) *Attorney, Agent, or Firm* — Birch, Stewart, Kolasch & Birch, LLP (57) ABSTRACT

The present invention provides the following: a cardiovascular disease primary prevention agent, which comprises as the active ingredient at least one selected from the group consisting of EPA, salts thereof, and esters thereof and is for lowering the risk of cardiovascular disease by administration to subjects having a blood (serum or plasma) hs-CRP level of 1.0 mg/L or higher in spite of no history of cardiovascular disease; a combination marker comprising the blood hs-CRP value and serum EPA/AA ratio for evaluating the primary risk of cardiovascular disease in subjects having no history of cardiovascular disease; and a method for extracting subjects with high risk of cardiovascular disease and/or a method for preventing cardiovascular disease.

11 Claims, 2 Drawing Sheets

(56) References Cited

OTHER PUBLICATIONS

Yokoyama et al., "Effects of eicosapentaenoic acid on major coronary events in hypercholesterolaemic patients (JELIS): a randomised open-label, blinded endpoint analysis", Articles, vol. 369, Mar. 31, 2007, pp. 1090-1098.

CARDIOVASCULAR DISEASE PRIMARY PREVENTION AGENT FOR PATIENTS HAVING HIGH BLOOD LEVELS OF HIGH-SENSITIVITY C-REACTIVE PROTEIN

TECHNICAL FIELD

This invention relates to an agent for primary prevention of cardiovascular disease, a marker for evaluating the risk of the cardiovascular disease, a method for extracting subjects having high risk of cardiovascular disease, and/or a method for primary prevention of cardiovascular disease.

BACKGROUND ART

Cardiovascular diseases are diseases which are leading causes of death in advanced countries. Primary and secondary prevention of this disease is a national health issue of importance, and recently, importance of the primary prevention which prevents the disease before the onset is widely recognized.

Cardiovascular diseases such as coronary artery diseases and cerebral stroke have common pathological background of arteriosclerosis, and risk factors of the arteriosclerosis include smoking, dyslipidemia (hyperlipidemia), hypertension, diabetes, obesity, lack of exercise, and the like. Accordingly, minimization of these risk factors is important in reducing the risk of the onset of cardiovascular diseases.

Accumulated investigations have proven that onset and progress of the arteriosclerosis is induced by the overlapping of a plurality of risk factors. The most important risk factor is dyslipidemia.

According to "Guidelines for Prevention of Atherosclerotic Cardiovascular Diseases 2012" (Non-patent literature 1), goals are set for the patients diagnosed with dyslipidemia depending on the control division based on the risk (absolute risk) of suffering from atherosclerotic diseases (namely, coronary artery disease, cerebral stroke, and arteriosclerosis obliterans based on atherosclerosis). More specifically, the control division is set by stratification based on the presence and absence of the additional risk of diabetes, chronic kidney disease, noncardiogenic cerebral infarction, and peripheral arterial disease. According to this guideline, life style is first improved and the adaptation of pharmacotherapy is then considered in the case of the primary prevention (the case with no history of the onset of coronary artery disease), while pharmacotherapy is considered together with the improvement of the life style in the case of the secondary prevention (the case with the history of the onset of the coronary artery disease).

Most typical therapeutic agents for dyslipidemia (in particular, high low density lipoprotein (hereinafter also referred to as "LDL") cholesterolemia) used for pharmacotherapy are statin drugs (inhibitors for hydroxymethylglutaryl-CoA (hereinafter also referred to as "HMG-CoA") reductase). The statin drugs which emerged in late 1980's are now sold in more than a hundred countries, and these drugs are said to be administered to at least 30 million people per day. Non-patent literature 1 describes that use of statin drug is recommended for high LDL cholesterolemia, and administration of eicosapentaenoic acid (hereinafter also referred to as "EPA") is considered in the case of dyslipidemia with high risk of cardiovascular disease as in the case of complication with diabetes or hypertension. The EPA preparation contains high purity ethyl eicosapentaenoate ester (hereinafter also referred to as "EPA-E") which has been extracted, for example, from sardine oil, esterified, and purified as an effective component, and it has the action of reducing blood neutral fat as well as the action of inhibiting intravascular thrombus formation through suppression of the aggregatory action of the platelet.

Patent Literature 1 describes a composition for preventing recurrence of cardiovascular events containing the EPA-E as an effective component which is useful for the prevention of the recurrence (secondary prevention) of the cardiovascular event, and in particular, which is expected to have a preventive effect for the cardiovascular event that recurs despite the therapy using the HMG-CoA reductase inhibitor and the recurrence of cardiovascular event that takes place after the passage of the unstable period after the cardiovascular reconstruction in the hyperlipidemia patient.

Patent Literature 2 describes a composition for preventing recurrence of cerebral stroke containing the EPA-E as an effective component which is useful in preventing the recurrence (secondary prevention) of the cerebral stroke, and more particularly, which is expected to have a preventive effect for the cerebral stroke that recurs despite the therapy using the HMG-CoA reductase inhibitor and the recurrence of cerebral stroke that takes place after 6 month or more after the onset of the cerebral stroke in the hyperlipidemia patient.

Non-Patent Literature 2 describes that, in the evaluation of the prevention of incipiency (primary prevention) of coronary artery disease for about 5 years, 18% decrease was found for the group of hypercholesterolemia patients having the EPA-E and the statin drug administered, although this result was not significant in terms of the risk compared to the group of patients with single administration of the statin drug.

However, it was not clear whether the EPA preparation was effective as an agent for primary prevention of cardiovascular disease irrespective of the suffering from dyslipidemia and/or the administration of the HMG-CoA reductase inhibitor preparation. Test items and reference values for the administration were also unclear.

In the meanwhile, Non-Patent Literature 3 discloses that ratio of the concentration of EPA to the concentration of arachidonic acid (hereinafter also referred to as "AA") in the plasma total lipid (hereinafter also referred to as "EPA/AA ratio") is expected for its use as a new bio-marker for the risk of cardiovascular death based on the results of an epidemiologic study. Non-Patent Literature 4 describes that the value of serum high sensitivity C reactive protein (hereinafter also referred to as "hs-CRP") is expected for its use as a new bio-marker for the risk of the onset of the cardiovascular disease also based on the results of an epidemiologic study. However, it has been unclear whether appropriate evaluation for the risk of the cardiovascular disease, and in particular, the risk of incipiency (hereinafter also referred to as "primary risk") of the cardiovascular disease is possible.

CITATION LIST

Patent Literature

Patent Literature 1: JP 2007-39452 A
Patent Literature 2: JP 2007-238594 A

Non-Patent Literature

Non-Patent Literature 1: Edited by Japan Atherosclerosis Society, "Guidelines for Prevention of Atherosclerotic Cardiovascular Diseases 2012", Jun. 20, 2012
Non-Patent Literature 2: The Lancet, 369, 1090-1098, 2007

Non-Patent Literature 3: The 75th Annual Scientific Meeting of the Japanese Circulation Society, Abstract and program (CD-ROM), OJ-140, 2011

Non-Patent Literature 4: Arteriosclerosis, Thrombosis, and Vascular Biology, 28, 1385-1391, 2008

SUMMARY OF INVENTION

Technical Problems

An object of the present invention is to provide an agent for primary prevention of cardiovascular disease, a marker for evaluating primary risk of cardiovascular disease, a method for extracting the subject with high risk of cardiovascular disease, and/or a method for primary prevention of cardiovascular disease.

Solution to Problems

In order to achieve the object as described above, the inventors of the present invention carried out an intensive study, and found in the epidemiologic study examining the association of the serum EPA/AA ratio with primary risk of cardiovascular disease in the group with no history of cardiovascular disease, while there is no association between the serum EPA/AA ratio and the primary risk of cardiovascular disease in the group with a serum hs-CRP value of less than 1.0 mg/L, in the group a the serum hs-CRP value of at least 1.0 mg/L, the primary risk of cardiovascular disease increases with the decrease in the serum EPA/AA ratio, and namely, there is a significant difference between the group with a serum hs-CRP value of less than 1.0 mg/L and the group with a serum hs-CRP value of at least 1.0 mg/L; and that in the group with a serum hs-CRP value of at least 1.0 mg/L, the primary risk of cardiovascular disease significantly increases at the serum EPA/AA ratio of less than 0.50. The inventors of the present invention also found that, in the subjects with no history of cardiovascular disease with a serum hs-CRP value of at least 1.0 mg/L, administration of the EPA-E results in the decrease of the onset risk of cardiovascular disease, and such effect is found irrespective of the administration of the statin drug. In other words, it has been found that the risk of new onset of cardiovascular disease can be reduced by the EPA-E administration in the subject having a serum hs-CRP value of at least 1.0 mg/L irrespective of whether the patient has dyslipidemia or not, for example, whether the value of the blood LDL cholesterol is within the therapeutic range. The present invention has been completed on the bases of such findings, and more specifically, the present invention is as described below.

(1) An agent for primary prevention of cardiovascular disease which is administered to a subject with no history of cardiovascular disease having a serum or plasma hs-CRP value (hereinafter also referred to as "blood hs-CRP value" or "hs-CRP value") of at least 1.0 mg/L for reducing risk of cardiovascular disease, wherein the agent comprises at least one member selected from the group consisting of EPA, its salts, and its esters as an effective component.

(2) The agent for primary prevention of cardiovascular disease according to the above (1), wherein the subject has an EPA/AA ratio in the total lipid of serum or plasma (hereinafter also referred to as "serum EPA/AA ratio" or "EPA/AA ratio") of less than 0.50.

(3) The agent for primary prevention of cardiovascular disease according to the above (2), wherein the serum EPA/AA ratio is less than 0.25.

(4) The agent for primary prevention of cardiovascular disease according to any one of the above (1) to (3) wherein the agent is administered to the subject and effective irrespective of whether the subject suffers from dyslipidemia.

(5) The agent for primary prevention of cardiovascular disease according to the above (4), wherein the dyslipidemia is high LDL cholesterolemia.

(6) The agent for primary prevention of cardiovascular disease according to any one of the above (1) to (5), wherein the agent is administered to the subject and effective irrespective of whether the subject is being administered with HMG-CoA reductase inhibitor.

(7) The agent for primary prevention of cardiovascular disease according to any one of the above (1) to (6), wherein the at least one member selected from the group consisting of EPA, its salts, and its esters is EPA-E.

(8) The agent for primary prevention of cardiovascular disease according to any one of the above (1) to (7) further comprising at least one member selected from the group consisting of docosahexaenoic acid (hereinafter also referred to as "DHA"), its salts, and its esters.

(9) The agent for primary prevention of cardiovascular disease according to the above (8), wherein the at least one member selected from the group consisting of DHA, its salts, and its esters is ethyl docosahexaenoate ester (hereinafter also referred to as "DHA-E").

(10) The agent for primary prevention of cardiovascular disease according to any one of the above (1) to (9), wherein the cardiovascular disease is coronary artery disease or cerebral stroke.

(11) The agent for primary prevention of cardiovascular disease according to the above (10), wherein the cardiovascular disease is myocardial infarction or angina.

(12) The agent for primary prevention of cardiovascular disease according to the above (10), wherein the cerebral stroke is cerebral infarction or cerebral hemorrhage.

(13) A combined marker for evaluating primary risk of cardiovascular disease of a subject who has no history of cardiovascular disease, wherein the marker comprises a blood hs-CRP value and a serum EPA/AA ratio.

(14) The combined marker according to the above (13), wherein the risk of cardiovascular disease is evaluated to be high when the hs-CRP value is at least 1.0 mg/L and the EPA/AA ratio is less than 0.50.

(15) The combined marker according to the above (13), wherein the risk of cardiovascular disease is evaluated to be ultra-high when the hs-CRP value is at least 1.0 mg/L and the EPA/AA ratio is less than 0.25, and the risk of cardiovascular disease is evaluated to be high when the hs-CRP value is at least 1.0 mg/L and the EPA/AA ratio is at least 0.25 and less than 0.50.

(16) The combined marker according to any one of the above (13) to (15), wherein the cardiovascular disease is coronary artery disease or cerebral stroke.

(17) The combined marker according to the above (16), wherein the cardiovascular disease is myocardial infarction or angina.

(18) The combined marker according to the above (16), wherein the cerebral stroke is cerebral infarction or cerebral hemorrhage.

(19) A method for extracting a subject with high risk of cardiovascular disease, comprising the steps of:
measuring a blood hs-CRP value of a subject;
measuring a serum EPA/AA ratio of the subject; and
extracting a subject with high risk of cardiovascular disease by combining the blood hs-CRP value and the serum EPA/AA ratio.

(20) A method for extracting a subject with high risk of cardiovascular disease, including the steps of measuring a blood hs-CRP value of a subject and measuring a serum EPA/AA ratio of the subject, the method comprising the step of:

extracting a subject with high risk of cardiovascular disease by combining the blood hs-CRP value and the serum EPA/AA ratio.

(21) The method for extracting a subject with high risk of cardiovascular disease according to the above (19) or (20), wherein the subject having the hs-CFP value of at least 1.0 mg/L and the EPA/AA ratio of less than 0.50 is extracted as a high risk subject of cardiovascular disease.

(22) The method for extracting a subject with high risk of cardiovascular disease according to the above (19) or (20), wherein the subject having the hs-CRP value of at least 1.0 mg/L and the EPA/AA ratio of less than 0.25 is extracted as a high risk subject of cardiovascular disease, and a subject having the hs-CRP value of at least 1.0 mg/L and the EPA/AA ratio of at least 0.25 and less than 0.50 is extracted as a high risk subject of cardiovascular disease.

(23) The method according to any one of the above (19) to (21), wherein the subject has no history of cardiovascular disease.

(24) An assay kit for use in the method of any one of the above (19) to (23) including at least means for measuring a blood hs-CRP value.

(25) A method for primary prevention of cardiovascular disease comprising the step of administering the agent for primary prevention of cardiovascular disease of any one of the above (1) to (12) to the subject extracted by the method of the above (23).

Advantageous Effects of Invention

The present invention provides a marker for evaluating the primary risk of cardiovascular disease; a method for extracting a subject with high risk of cardiovascular disease; an agent for primary prevention of cardiovascular disease comprising at least one member selected from the group consisting of EPA, its salts, and its esters as an effective component which is administered to subjects having no history of cardiovascular disease with a blood hs-CRP value of at least 1.0 mg/L to thereby reduce the risk of cardiovascular disease; and/or a method for primary prevention of cardiovascular disease.

The agent for primary prevention of cardiovascular disease of the present invention can be administered to both the patient receiving the statin drug and the patient not receiving the statin drug, and it can reduce the risk of cardiovascular disease in the subject having no history of cardiovascular disease with a blood hs-CRP value of at least 1.0 mg/L.

The agent for primary prevention of cardiovascular disease of the present invention can be administered to both patients suffering from dyslipidemia (hyperlipidemia) and subjects who have never been diagnosed with the dyslipidemia (hyperlipidemia), irrespective of the type and seriousness of the dyslipidemia and irrespective of whether the subject is receiving a statin drug, to thereby reduce the risk of cardiovascular disease in the subjects with no history of cardiovascular disease with a blood hs-CRP value of at least 1.0 mg/L.

The marker for evaluating the risk of cardiovascular disease of the present invention is capable of evaluating the risk of cardiovascular disease at a high precision and objectively by using the blood hs-CRP value and the serum EPA/AA ratio.

When the marker for evaluating primary risk of cardiovascular disease of the present invention is used, subjects with high primary risk of cardiovascular disease requiring the administration of the agent for primary prevention of cardiovascular disease of the present invention can be extracted.

By using the method for primary prevention of cardiovascular disease of the present invention, the primary prevention of cardiovascular disease can be accomplished for the subject with no history of cardiovascular disease but having high primary risk of cardiovascular disease with a blood hc-CRP value of at least 1.0 mg/L, irrespective of whether the subject has dyslipidemia (hyperlipidemia), irrespective of the type and seriousness of the dyslipidemia, and irrespective whether the subject is receiving the administration of a statin drug. The method for primary prevention of cardiovascular disease of the present invention is also a method effective for detecting subjects with high risk of cardiovascular disease at an early stage to thereby reduce the risk of cardiovascular disease in the subjects who are already receiving a statin drug and experiencing some therapeutic effects for the dyslipidemia.

DESCRIPTION OF EMBODIMENTS

Next, the present invention is described in detail.

[Agent for Primary Prevention of Cardiovascular Disease]

The agent for primary prevention of cardiovascular disease of the present invention comprises at least one member selected from the group consisting of EPA, its salts, and its esters as an effective component, and the agent is used for reducing the risk of cardiovascular disease by administering the agent to a subject who has no history of cardiovascular disease and has a blood hs-CRP value of at least 1.0 mg/L.

<Cardiovascular Disease>

In the present invention, the cardiovascular diseases include coronary artery diseases, cerebral strokes (cerebrovascular disorders), and peripheral vascular diseases, and preferably, coronary artery diseases and cerebral strokes, and more preferably, coronary artery diseases. The coronary artery diseases include, for example, myocardial infarction and angina, and cerebral strokes include, for example, cerebral infarction and cerebral hemorrhage.

In the present invention, "no history of cardiovascular disease" means that the subject has no history of the onset of coronary artery disease, cerebral stroke (cerebrovascular disorders), or peripheral vascular disease, and more specifically, that the subject has no history of the definite diagnosis of the coronary artery disease such as myocardial infarction and angina, and cerebrovascular disease such as cerebral infarction and cerebral hemorrhage. In addition, when a cardiovascular event took place at a cardiovascular site different from the site responsible for the onset of a past cardiovascular disease, the event can be categorized as an incipient cardiovascular disease, and in a broad sense, the onset of a cardiovascular event of such a patient can be regarded as the onset of a cardiovascular event of the patient with no history of cardiovascular disease.

<Subjects>

In the present invention, the agent for primary prevention of the present invention is administered to a subject with no history of cardiovascular disease having a blood hs-CRP value of at least 1.0 mg/L, at least 1.5 mg/L, or at least 2.0 mg/L. In addition, the agent for primary prevention of the present invention can be administered to any subject as long as the conditions as described above are satisfied irrespective of whether the subject suffers from other diseases or whether the subject is administered with other drugs.

<<Method Used for Measuring Blood hs-CRP Value>>

The method used for measuring the blood hs-CRP is not particularly limited as long as it is a high sensitivity CRP measurement method capable of measuring the C reactive protein (CRP) of at least 0.1 mg/L, preferably at least 0.05 mg/L, and more preferably 0.01 mg/L. Exemplary such high sensitivity CRP measurement methods include ELISA, latex nephelometry, laser nephelometry, and improved latex immunonephelometry. Exemplary ELISA methods include Banalyst Ace hsCRP (SANWA KAGAKU KENKYUSHO CO., LTD., Nagoya, Japan), ELISA Kit High Sensitivity C-Reactive Protein (immuno-Biological Laboratories, Inc., Minnesota, USA), and hsCRP Human ELISA (BioVendor, Heidelberg, Germany). Exemplary latex nephelometry methods include N-latex CRP II (Siemens Healthcare Diagnostics, Tokyo, Japan), and the improved latex immunonephelometry may be conducted by using a commercially available assay kit such as Vitros microchip hsCRP (Ortho Clinical Diagnostics, Tokyo, Japan).

<<Serum EPA/AA Ratio and Method Used for its Measurement>>

The serum EPA/AA ratio is the ratio in concentration (unit: μg/mL) of the EPA to the AA in the serum total lipid. However, this serum EPA/AA ratio also refers to the ratio in concentration (unit: μg/mL) of the EPA to the AA in the plasma total lipid. It can also be described in terms of the ratio in molar concentration (unit: mol/mL) of the EPA to the AA in the serum total lipid or plasma total lipid.

The serum EPA/AA ratio of the target subject is not particularly limited. The serum EPA/AA ratio is preferably less than 0.50, more preferably less than 0.40, still more preferably less than 0.25, still more preferably less than 0.20, and most preferably less than 0.10.

The method used for measuring the EPA and AA is not particularly limited, and exemplary methods include hydrolysis of the serum or the plasma followed by the analysis of the EPA and AA in the total lipid by gas chromatography (GC), gas chromatography-mass spectrometry (GC-MS), or GC×GC-MS.

<<Other Diseases>>

Exemplary other diseases include dyslipidemia (hyperlipidemia), hypertension, diabetes, chronic kidney disease, noncardiogenic cerebral infarction, and peripheral arterial disease.

Exemplary dyslipidemia include hypercholesterolemia, high LDL cholesterolemia, low high density lipoprotein (HDL) cholesterolemia, low non-HDL cholesterolemia, hyperapolipoprotein-B-emia, high lipoprotein-associated phospholipase A2-emia, and hypertriglyceridemia.

<<Other Drugs>>

Typical other drugs include therapeutic agents for dyslipidemia.

Exemplary therapeutic agents for dyslipidemia include inhibitors for cholesterol synthesis (HMG-CoA reductase inhibitor (statin drugs)), promoter for cholesterol catabolism (probucol etc.), inhibitors for cholesterol absorption (cholestyramine etc. (anion-exchange resin)), inhibitors for triglyceride (TG) synthesis (fibrate drugs), and inhibitors for intestinal cholesterol transporter (ezetimibe etc.).

<Effective Components>

The agent for primary prevention of cardiovascular disease of the present invention comprises at least one member selected from the group consisting of the EPA, its salts, and its esters as its effective component. Content of the effective component selected from the group consisting of the EPA, its salts, and its esters in relation to the total amount of the fatty acid (including its salts and esters) in the agent for primary prevention of cardiovascular disease of the present invention is preferably at least 40% by weight, more preferably at least 60% by weight, still more preferably at least 80% by weight, still more preferably at least 90% by weight, still more preferably at least 95% by weight, still more preferably 96.5% by weight, still more preferably at least 97% by weight, and still more preferably at least 98% by weight, and in other words, the higher content is preferable.

The EPA is all-cis-5,8,11,14,17-icosapentaenoic acid (all-cis-5,8,11,14,17-icosapentaenoic acid) or (5Z,8Z,11Z,14Z,17Z)-icosa-5,8,11,14,17-pentaenoic acid.

The salt of EPA is not particularly limited. However, the preferred is sodium salt (hereinafter also referred to as "EPA-Na").

The ester of EPA is not particularly limited. However, the preferred are glyceride ester and ethyl ester, and the more preferred is the ethyl ester.

Of the EPA, its salts, and its esters, the preferred is the EPA-E.

The at least one member selected from the group consisting of the EPA, its salts, and its esters is more preferably EPA-E.

<Long Chain Unsaturated Fatty Acid Other than the Effective Components>

The agent for primary prevention of cardiovascular disease of the present invention may further comprise a long chain unsaturated fatty acid other than the effective component as described above, and in particular, an ω-3 long chain unsaturated fatty acid, and preferably an ω-3 long chain polyunsaturated fatty acid.

Examples of such ω-3 long chain polyunsaturated fatty acid include at least one member selected from the group consisting of DHA, its salts, and its esters, and such ω-3 long chain polyunsaturated fatty acid may be incorporated preferably at a content of up to 60% by weight, more preferably up to 40% by weight, still more preferably up to 20% by weight, still more preferably up to 10% by weight, still more preferably up to 5% by weight, still more preferably up to 3.5% by weight, still more preferably up to 3% by weight, still more preferably up to 2% by weight, and still more preferably up to 0.3% by weight (namely, preferably at a lower content rate) in relation to the total content of the fatty acid (including its salts and esters) in the agent for primary prevention of cardiovascular disease of the present invention.

The total content of the ω-3 long chain polyunsaturated fatty acid (including its salts and esters) including the at least one member selected from the group consisting of EPA, its salts, and its esters is preferably at least 40% by weight, more preferably at least 70% by weight, still more preferably at least 80% by weight, still more preferably at least 90% by weight, still more preferably at least 95% by weight, still more preferably at least 96.5% by weight, still more preferably at least 97% by weight, and still more preferably at least 98% by weight (namely, preferably at a higher content rate) in relation to the total content of the fatty acid (including its salts and esters) in the agent for primary prevention of cardiovascular disease of the present invention.

The DHA is all-cis-4,7,10,13,16,19-docosahexaenoic acid (all-cis-4,7,10,13,16,19-docosahexaenoic acid) or (4Z,7Z, 10Z,13Z,16Z,19Z)-docosa-4,7,10,13,16,19-hexaenoic acid.

The salt of DHA is not particularly limited. However, the preferred is sodium salt (hereinafter also referred to as "DHA-Na").

The ester of DHA is not particularly limited. However, the preferred are glyceride ester and ethyl ester, and the more preferred is the ethyl ester.

Of the DHA, its salts, and its esters, the preferred is the DHA-E.

The at least one member selected from the group consisting of the DHA, its salts, and its esters is more preferably DHA-E.

Content of the ω-6 long chain unsaturated fatty acid, and in particular, the AA is preferably up to 5% by weight, more preferably up to 2% by weight, still more preferably up to 1% by weight, and still more preferably substantially free in relation to the total content of the fatty acid (including its salts and esters) in the agent for primary prevention of cardiovascular disease of the present invention.

<Other Optional Components>

In addition to the components as described above, the agent for primary prevention of cardiovascular disease of the present invention may also comprise a pharmaceutically acceptable excipient. Since both EPA and DHA are highly unsaturated, an antioxidant, for example, butylated hydroxytoluene, butylated hydroxyanisole, propylgallate, gallic acid, or a pharmaceutically acceptable quinone and α-tocopherol may be incorporated at an effective amount.

<Dosage Form>

Exemplary dosage forms include tablet, capsule, microcapsule, granules, fine granules, acid, oral liquid preparation, self-emulsifying preparation, emulsion, syrup, and jelly which are adapted for oral administration to the subject. The preferred is oral administration by incorporating in a capsule, for example, soft capsule or microcapsule.

Epadel® and Epadel® S are soft capsules containing high purity EPA-E which are commercially sold in Japan as a safe therapeutic agent for arteriosclerosis obliterans and hyperlipidemia with reduced side effects. Content of the EPA-E in total fatty acid is at least 96.5° by weight. Vascepa® (Amarin Pharmaceuticals, Inc.) is commercially available in the U.S. as a therapeutic agent for hypertriglyceridemia.

Soft capsules (Lovaza® (GlaxoSmithKline), Omacor® (Pronova), and Lotoriga® (Takeda Pharmaceutical Company)) containing about 46% by weight of EPA-E and about 38% by weight of DHA-E in total fatty acid are also commercially available in the U.S., Europe, and Japan as a therapeutic agent for hypertriglyceridemia.

The agent for primary prevention of cardiovascular disease used in the present invention may be a commercially available product. Preferable examples of such products containing the EPA-E and the DHA-E include Lovaza® Omacor®, and Lotoriga®, and the more preferred is use of those containing high purity EPA-E such as Epadel® and Vascepa® wherein content of the EPA-E in the total fatty acid is at least 96.5% by weight since such agents do not substantially contain AA.

<Dosage, Dosing Period>

The dosage and dosing period of the agent for primary prevention of cardiovascular disease of the present invention is the dosage and dosing period sufficient for realizing the effect of the primary prevention of cardiovascular disease, and they may be adequately adjusted by the dosage form, administration route, daily dosage frequency, body weight, age, and the like.

The dosage and dosing period of the agent for primary prevention of cardiovascular disease of the present invention are preferably decided so that the blood hs-CRP value reduces by at least 0.1 mg/L, preferably at least 0.25 mg/L, more preferably at least 0.5 mg/L, still more preferably at least 0.75 mg/L, still more preferably at least 1.0 mg/L, and still more preferably at least 1.5 mg/L compared to the value at the start of the treatment or the value in the previous measurement; or to retain the level of less than 2.0 mg/L, preferably less than 1.5 mg/L, more preferably less than 1.25 mg/L, still more preferably less than 1.0 mg/L, still more preferably less than 0.75 mg/L, and still more preferably less than 0.5 mg/L; and simultaneously that the serum EPA/AA ratio increases by at least 0.1, preferably at least 0.20, more preferably at least 0.25, still more preferably at least 0.40, still more preferably at least 0.50, and still more preferably at least 0.60 compared to the value at the start of the treatment or the value in the previous measurement; or to retain the level of at least 0.50, preferably at least 0.60, still more preferably at least 0.70, still more preferably at least 0.75, still more preferably at least 0.80, and still more preferably at least 1.0.

In the case of oral administration, the dose in terms of EPA-E is 0.1 to 10 g/day, preferably 0.3 to 6 g/day, more preferably 0.9 to 3.6 g/day, and still more preferably 1.8 to 2.7 g/day which is administered in 3 divided doses. However, if desired, entire dose may be administered at once, or in several divided doses. In the case of the oral administration, the dose in terms of the entire ω-3 long chain polyunsaturated fatty acid (including its salts and esters) is 0.1 to 10 g/day, preferably 0.3 to 9 g/day, more preferably 1 to 6 g/day, and still more preferably 2 to 4 g/day which is administered in 3 divided doses. However, if desired, entire dose may be administered at once, or in several divided doses.

Examples of dose per administration and daily frequency include 0.3 g (once a day), 0.3 g (twice a day), 0.3 g (3 to 10 times a day), 0.6 g (once a day), 0.6 g (twice a day), 0.6 g (3 to 10 times a day), 0.9 g (once a day), 0.9 g (twice a day), 0.9 g (3 to 10 times a day), 1 g (once a day), 1 g (twice a day), 1 g (3 to 10 times a day), 1.2 g (once a day), 1.2 g (twice a day), 1.2 g (3 to 8 times a day), 1.8 g (once a day), 1.8 g (twice a day), 1.8 g (3 to 5 times a day), 2 g (once a day), 2 g (twice a day), 2 g (3 to 5 times a day), 2.4 g (once a day), 2.4 g (twice a day), 2.4 g (3 to 4 times a day), 2.7 g (once a day), 2.7 g (twice a day), 2.7 g (3 times a day), 3 g (once a day), 3 g (twice a day), 3 g (3 times a day), 3.6 g (once a day), 3.6 g (twice a day), 4 g (once a day), 4 g (twice a day), 4.5 g (once a day), 4.5 g (twice a day), 5 g (once a day), 5 g (twice a day), 6 g (once a day), 7 g (once a day), 8 g (once a day), 9 g (once a day), 10 g (once a day), and adequate combinations of such dose and daily frequency.

The agent is preferably administered during the meal or after the meal, and more preferably, immediately after the meal (within 30 minutes after the meal). In the case of a self-emulsifying preparation, the timing of the administration is not particularly limited because of the excellent absorbability, and such preparation may also be administered, for example, before the meal, between the meals, or before going to bed. When the dose as described above is orally administered, the dosing period is at least 1 year, preferably at least 2 years, more preferably at least 3.5 year, and still more preferably at least 5 years, and the administration is preferably continued as long as the risk of the onset and/or recurrence of cardiovascular event is still high. In some cases, a drug withdrawal period of about 1 day to about 3 months, and preferably about 1 week to about 1 month may be incorporated.

[Marker for Evaluating the Risk of Cardiovascular Disease]

The combined marker for evaluating the risk of cardiovascular disease in the subject with no history of cardiovascular disease of the present invention includes both the blood hs-CRP value and the serum EPA/AA ratio.

<Blood High Sensitivity C Reactive Protein Value>

The blood high sensitivity C reactive protein value is also referred to as the blood high sensitivity CRP value or blood hs-CRP value, and it represents concentration (unit: mg/L) in blood (in serum or plasma) of the C reactive protein.

The hs-CRP value and the conventional C reactive protein value both represent concentration in blood of same protein (C reactive protein). However, the hs-CRP value is the value of the C reactive protein obtained by the method with higher sensitivity. While the measurement limit of a conventional method for C reactive protein measurement is about 1 mg/L, the measurement limit of a method for hs-CRP measurement is 0.1 mg/L, and preferably 0.01 mg/L.

The measurement may be conducted by a method such as ELISA and LA/nephelometry.

<Serum EPA/AA Ratio>

The serum EPA/AA ratio is a weight ratio of EPA to AA in serum total lipid.

The measurement is conducted by hydrolyzing serum or plasma, weighing each of the EPA and the AA in the total lipid, and dividing the weight of the EPA by the weight of the AA.

The weighing of the EPA and the AA may be conducted, for example, by gas chromatography (GC), gas chromatography/mass spectrometry (GC/MS), or FTIR (AOAC).

<Criteria for Evaluating Risk of Cardiovascular Disease>

The subject is evaluated to be a subject with high risk of cardiovascular disease when the blood hs-CRP value is at least 1.0 mg/L and the serum EPA/AA ratio is less than 0.50.

The subject may be evaluated to be a subject with ultra-high risk of cardiovascular disease when the blood hs-CRP value is at least 1.0 mg/L, and the serum EPA/AA ratio is less than 0.25, and a subject with high risk of cardiovascular disease when the blood hs-CRP value is at least 1.0 mg/L and the serum EPA/AA ratio is at least 0.25 and less than 0.50.

Furthermore, the subject may also be evaluated to be a subject with medium risk of cardiovascular disease when the blood hs-CRP value is at least 1.0 mg/L, and the serum EPA/AA ratio is at least 0.50.

The threshold of the serum EPA/AA ratio of less than 0.50 may be changed to any value in the range of less than 0.26 to less than 0.74, for example, less than 0.70, less than 0.60, less than 0.40, or less than 0.30. The threshold of the serum EPA/AA ratio of less than 0.25 may be changed to a value of, for example, less than 0.20 or less than 0.10.

The risk may also be evaluated as an increase when the blood hs-CRP value is reduced by at least 1.0 mg/L, and the serum EPA/AA ratio is reduced by at least 0.10, preferably at least 0.20, more preferably at least 0.25, still more preferably at least 0.30, still more preferably at least 0.40, and still more preferably at least 0.50 compared to the value in the previous measurement.

However, the serum EPA/AA ratio and the risk of cardiovascular disease are not associated when the blood hs-CRP value is less than 1.0 mg/L. The blood hs-CRP value of at least 1.0 mg/L used as the risk evaluation criterion as described above may be changed to at least 1.5 mg/L or at least 2.0 mg/L in evaluation.

An example of the combined marker of the present invention is a medium where the subject, the physician, and/or the like can simultaneously recognize both the blood hs-CRP value and the serum EPA/AA ratio, and more specifically, a medium where both the blood hs-CRP value the serum EPA/AA ratio are described or recorded, and more preferably, where the measurement of both the blood hs-CRP value and the serum EPA/AA ratio are described or recorded together with the risk as described above evaluated by such combination. Exemplary mediums include paper medium and electronic recording medium.

At the moment, the association between the blood C reactive protein value and the serum EPA/AA ratio is not yet clear. EPA is said to have the effects such as improvement of the dysfunction of the vascular endothelium, platelet aggregation inhibition, stabilization of plaque by the anti-inflammatory action. On the other hand, the AA is said to produce physiologically active substances having a strong ability of platelet aggregation and strong inflammation inducing substances.

In addition, since increase in the blood C reactive protein value is a risk factor for cardiovascular disease, significant correlation between the serum EPA/AA ratio and the risk of cardiovascular disease was recognized in the present invention for the group with a high blood C reactive protein value (high hs-CRP group; blood CRP value≥1.0 mg/L).

[Method for Extracting Subjects with High Risk of Cardiovascular Disease]

The first embodiment of the method for extracting the subject with high risk of cardiovascular disease of the present invention is a method comprising the steps of measuring the blood hs-CRP value of a subject, measuring the serum EPA/AA ratio of the subject, and extracting a subject having high risk of cardiovascular disease by combining the blood hs-CRP value and the serum EPA/AA ratio.

The second embodiment of the method for extracting the subject with high risk of cardiovascular disease of the present invention is a method including the steps of measuring the blood hs-CRP value of a subject and measuring the serum EPA/AA ratio of the subject, the method comprising the step of:

extracting a subject having high risk of cardiovascular disease by combining the blood hs-CRP value and the serum EPA/AA ratio.

More specifically, the first and second embodiments as described above are a method comprising the step of extracting a subject having high risk of cardiovascular disease or a subject having ultra-high risk of cardiovascular disease when the blood hs-CRP value is at least 1.0 mg/L, and the serum EPA/AA ratio is below a particular value, for example, less than 0.50 or less than 0.25.

The threshold of the serum EPA/AA ratio of less than 0.50 may be changed to any value in the range of less than 0.26 to less than 0.74. The method includes the step of extracting the subject with the risk of vascular disease, where the threshold of the serum EPA/AA ratio is, for example, less than 0.70, less than 0.60, less than 0.40, or less than 0.30. In addition, the method includes the step of extracting the subject with the risk of vascular disease, where the threshold of the serum EPA/AA ratio of less than 0.25 is changed to, for example, less than 0.20 or less than 0.10.

The blood hs-CRP value of at least 1.0 mg/L in the method for extracting as described above may be changed to at least 1.5 mg/L or at least 2.0 mg/L.

[Assay Kit for Extracting Subjects with Risk of Cardiovascular Disease]

The assay kit of the present invention is an assay kit for use in the method for extracting the subject with high risk of cardiovascular disease, and the kit at least contains means for measuring the blood hs-CRP value.

Since the hs-CRP value is determined by means of, for example, ELISA, latex nephelometry, laser nephelometry, improved latex immunonephelometry, or the like as described above, the reagents used in these assay methods are preferably included in the kit.

[Method for Primary Prevention of Cardiovascular Disease for Subjects with High Risk of Cardiovascular Disease]

This method is a method in which the subject with high risk of cardiovascular disease is first extracted by the method as described above, and the agent for primary prevention of cardiovascular disease of the present invention is then administered to such a subject to thereby reduce the risk of the onset of cardiovascular disease. In the preventive method of the present invention, as an index of reducing the risk of the onset, the method may be accomplished by aiming at reducing the blood hs-CRP value by at least 0.1 mg/L, preferably at least 0.25 mg/L, more preferably at least 0.5 mg/L, still more preferably at least 0.75 mg/L, still more preferably at least 1.0 mg/L, and still more preferably at least 1.5 mg/L compared to the value at the start of the treatment or the value in the previous measurement; or retaining the blood hs-CRP value at the level of less than 2.0 mg/L, preferably less than 1.5 mg/L, more preferably less than 1.25 mg/L, still more preferably less than 1.0 mg/L, still more preferably less than 0.75 mg/L, and still more preferably less than 0.5 mg/L; and simultaneously, increasing the serum EPA/AA ratio by at least 0.1, preferably at least 0.20, more preferably at least 0.25, still more preferably at least 0.40, still more preferably at least 0.50, and still more preferably at least 0.60 compared to the value at the start of the treatment or the value in the previous measurement; or retaining the serum EPA/AA ratio at the level of at least 0.50, preferably at least 0.60, more preferably at least 0.70, still more preferably at least 0.75, still more preferably at least 0.80, and still more preferably at least 1.0.

If desired, an HMG-CoA reductase inhibitor (statin drugs) or other therapeutic agent for dyslipidemia, therapeutic agent for hypertension, antidiabetic drug, therapeutic agent for chronic kidney disease, therapeutic agent for noncardiogenic cerebral infarction, therapeutic agent for peripheral arterial disease, or the like may be mixed with or used in combination with the agent for primary prevention of cardiovascular disease of the present invention to simultaneously realize the effects of the HMG-CoA reductase inhibitor or other therapeutic agent for dyslipidemia, therapeutic agent for hypertension, antidiabetic drug, therapeutic agent for chronic kidney disease, therapeutic agent for noncardiogenic cerebral infarction, therapeutic agent for peripheral arterial disease, or the like.

The method of the present invention is effective also for a patient whose LDL cholesterol has been maintained at a particular value (for example, less than 120 mg/dL, less than 100 mg/dL, or less than 80 mg/dL) by the administration of a statin drug. In particular, the subject with high risk of cardiovascular disease is extracted by the method as described above from the patients who have already been administered with the statin drug with the lipid level in the normal range and whose treatment has apparently succeeded, and the risk of new onset of cardiovascular disease can be reduced by using the agent for primary prevention of the present invention.

EXAMPLES

1. Summary of Epidemiologic Study

In this Example, the inventors examined the association between the serum EPA/AA ratio and the risk of the onset and death of and from cardiovascular disease as a part of the Hisayama study.

The Hisayama study is an epidemiologic study of cerebral stroke, cardiovascular disease, and the like that has been conducted with the residents of the town of Hisayama town (population, about 8,400) in Kasuya county of Fukuoka prefecture adjacent to Fukuoka city from 1961. The age and occupation distributions of the residents of Hisayama town were almost identical to those of Japan as a whole, and the residents can be regarded as an average group of Japanese people with substantially no bias. Features of the Hisayama study include participation of all residents (who are at least 40 years old), prospective cohort study, examination and home visit by the stuff of the study, consultation rate (at least 80%), autopsy rate (about 80%), and follow-up rate (at least 99%), and the most characteristic feature of this study is the high rate of autopsy. No diagnosis is more accurate than autopsy in finding out the accurate cause of the death, and the precision of the follow up study is also high. In addition, the Hisayama study periodically adds the residents who have reached 40 years old to the group every 5 years, and estimation of influence of the life style transition as well as change of risk factors was thereby enabled.

2. Subject and Follow-Up Period 3,103 residents of 40 years old or older who were registered in 2002 were used for the subject excluding those who have history of cardiovascular disease and those with no data of EPA/AA ratio. Average follow-up period was 5.1 years.

Of the 3,103 subjects, death cases were 191 cases in total. Of these, the causes of the death included 48 cases of cardiovascular disease (International Statistical Classification of Diseases and Related Health Problems, 10th Revision (ICD10):I00-I99), 70 cases of cancer (ICD10:C00-D48), 39 cases of infectious disease (ICD10:A00-B99, J00-J39, J69, N13.6), and 34 cases of other causes. 127 cases of the onset of cardiovascular disease (alive/dead) were found, and of these, the onset of coronary artery disease was 49 cases, and the onset of cerebral stroke was 83 cases.

3. Analysis (1) Serum EPA/AA Ratio

The serum EPA/AA ratio of the subject was determined by collecting blood from the subjects, conducting hydrolysis of the serum or plasma, quantitating the EPA and the AA in the total lipid by gas chromatography to measure the concentration (unit: μg/mL), and calculating the ratio in concentration of the EPA to the AA.

(2) hs-CRP Value

The blood hs-CRP value of the subject was determined by collecting blood from the subjects, treating the sample by a commercially available high sensitivity CRP assay latex reagent, and conducing the assay by a biochemical automatic analysis system (unit: mg/L).

4. Relation Between Serum EPA/AA Ratio and Total Deaths and Cardiovascular Deaths The relation between the serum EPA/AA ratio and the total deaths and cardiovascular deaths was analyzed by using Cox proportional hazard model with potential confounders such as age and sex being adjusted. The total death risks were respectively 23.5, 11.8, 12.8, and 11.5 person-years per 1000 person-years in the groups with the serum EPA/AA ratios of less than 0.25, 0.25 to 0.49, 0.5 to 0.74, and 0.75 or higher (p value in the trend analysis=0.01). Similarly, the cardiovascular death risk increased with the decrease in the serum EPA/AA ratio, and the risks were respectively 4.9, 4.0, 2.2, and 1.6 person-years per 1000 person-years in the groups with the serum EPA/AA ratios of less than 0.25, 0.25-0.49, 0.5-0.74, and 0.75 or higher (p value in the trend analysis=0.03). In other words, the total death risk and the cardiovascular death risk of the subjects with a serum EPA/AA ratio of less than 0.25 were respectively 2.04-fold and 3.06-fold higher than the subjects with a serum EPA/AA ratio of at least 0.75.

In the meanwhile, a hazard ratio was calculated by using Cox proportional hazard model with use of the entire subjects as the standard (1.00). The risk was adjusted for potential confounders such as age, sex, hypertension, diabetes, serum total cholesterol, use of therapeutic agent for dyslipidemia, BMI (body mass index), smoking habit, and alcohol ingestion. For the entire subject group, after the adjustment of the potential confounders, it has been found that the risk of the cardiovascular death increases by 1.44-fold with every decrease in the serum EPA/AA ratio of 0.25, while the risk of cancer death, the risk of infection death, and the risk of death by other causes respectively increase by 1.10-fold, 1.05-fold, and 1.03-fold with every decrease in the serum EPA/AA ratio of 0.25, i.e., are not substantially affected.

5. Relation Between the Serum EPA/AA Ratio and the hs-CRP Value

The 3,103 subjects were divided into 2 groups, namely, the group with a blood hs-CRP value of less than 1.0 mg/L (low hs-CRP group) and the group with a blood hs-CRP value of at least 1.0 mg/L (high hs-CRP group). Each of these groups was further divided into 4 groups, namely, the group with a serum EPA/AA ratio of less than 0.25, the group with a serum EPA/AA ratio of 0.25 to 0.49, the group with a serum EPA/AA ratio of 0.50 to 0.74, and the group with a serum EPA/AA ratio of 0.75 or higher.

The number of subjects in each group divided by the blood hs-CRP value and the serum EPA/AA ratio are as shown in the column of "n" in Table 1 and Table 2.

For each of the low hs-CRP group and the high hs-CRP group, the hazard ratio of each group (namely, each of the groups having respective serum EPA/AA ratios of 0.50 to 0.74, 0.25 to 0.49, and less than 0.25) to the group with a serum EPA/AA ratio of at least 0.75 was calculated by using Cox proportional hazard model. The risk was adjusted for potential confounders such as age, sex, hypertension, diabetes, serum total cholesterol, use of therapeutic agent for dyslipidemia, BMI (body mass index), smoking habit, and alcohol ingestion. The resulting hazard ratios are shown in the column of "hazard ratio" in Table 1 and Table 2.

Figure 1:
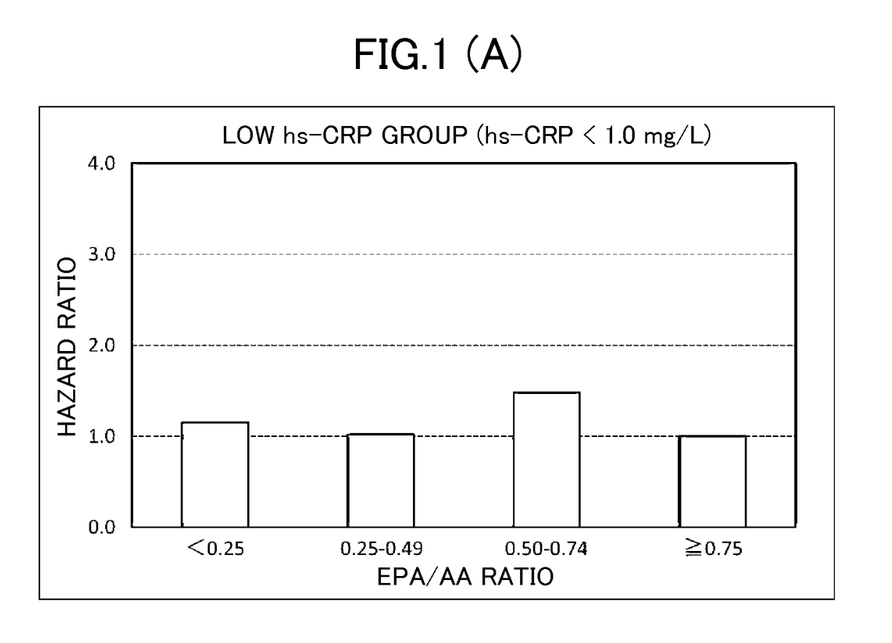
FIG. 1(A) is a graph showing the relation between the serum EPA/AA ratio and the hazard ratio of the group with a blood hs-CRP value of less than 1.0 mg/L (low hs-CRP group).
FIG. 1(B) is a graph showing the relation between the serum EPA/AA ratio and the hazard ratio of the group with a blood hs-CRP value of at least 1.0 mg/L (high hs-CRP group).

FIG. 1 includes (A) a bar graph showing the hazard ratio of the low hs-CRP group and (B) a bar graph showing the hazard ratio of the high hs-CRP group.

TABLE 1

| | EPA/AA ratio | n | Hazard ratio |
|---|---|---|---|
| Low hs-CRP group (<1.0 mg/L) | <0.25 | 414 | 1.15 |
| | 0.25 to 0.49 | 1058 | 1.02 |
| | 0.50 to 0.74 | 564 | 1.48 |
| | ≥0.75 | 273 | 1.00 |

In the low hs-CRP group, no significant association between the serum EPA/AA ratio and the hazard ratio was recognized.

TABLE 2

| | EPA/AA ratio | n | Hazard ratio |
|---|---|---|---|
| High hs-CRP group (≥1.0 mg/L) | <0.25 | 137 | 3.39 |
| | 0.25 to 0.49 | 348 | 2.32 |
| | 0.50 to 0.74 | 207 | 1.15 |
| | ≥0.75 | 102 | 1.00 |

On the other hand, in the high hs-CRP group (hs-CRP≥1.0 mg/L), the hazard ratio significantly increased with the decrease of the serum EPA/AA ratio, and the hazard ratio was 2.32-fold higher in the group with a serum EPA/AA ratio of 0.25 to 0.49, and 3.39-fold higher in the group with a serum EPA/AA ratio of less than 0.25 compared with the group with a serum EPA/AA ratio of at least 0.75.

As evident from the results as described above, the combined marker of the blood hs-CRP value and the serum EPA/AA ratio is effective as a marker for evaluating the risk of cardiovascular disease. The adequacy of evaluation of the group with a blood hs-CRP value of at least 1.0 mg/L and a serum EPA/AA ratio of less than 0.50 as the group with high risk of cardiovascular disease was also demonstrated. Furthermore, since the risk of the group with a blood hs-CRP value of at least 1.0 mg/L and a serum EPA/AA ratio of less than 0.25 was significantly higher than the group with a serum EPA/AA ratio of at least 0.25 and less than 0.50, the adequacy of evaluation of the group with a blood hs-CRP value of at least 1.0 mg/L and a serum EPA/AA ratio of less than 0.25 as the group with ultra-high risk of cardiovascular disease and evaluation of the group with a blood hs-CRP value of at least 1.0 mg/L and a serum EPA/AA ratio of at least 0.25 and less than 0.50 to be the group with high risk of cardiovascular disease was also demonstrated.

6. Relation Between Blood hs-CRP Value, 5 Year Incidence Rate, and Hazard Ratio

The subjects were divided into two groups, namely, the group with a blood hs-CRP value of at least 1.0 mg/L, and the group with a blood hs-CRP value of less than 1.0 mg/L. The blood hs-CRP value was quantitated by using a commercially available assay kit.

For each of the groups, 5 year incidence rate (incidence rate in 5 years) of cardiovascular disease, coronary artery disease, and cerebral stroke as well as the hazard ratio was determined. These values are indicated in the corresponding columns of Table 3. The hazard ratio was calculated by using Cox proportional hazard model with use of the entire subjects as the standard (1.00). The risk was adjusted for potential confounders such as age, sex, hypertension, diabetes, serum total cholesterol, use of therapeutic agent for dyslipidemia, BMI (body mass index), smoking habit, and alcohol ingestion.

TABLE 3

| hs-CRP | 5 year incidence rate | Hazard ratio (95% confidence interval) | p value |
|---|---|---|---|
| Cardiovascular disease (CVD) | | | |
| <1.0 mg/L | 3.5 | 0.94 (0.78 to 1.14) | 0.01 |
| ≥1.0 mg/L | 5.9 | 1.66 (1.14 to 2.42) | |
| Coronary artery disease (CHD) | | | |
| <1.0 mg/L | 1.3 | 0.93 (0.69 to 1.25) | 0.008 |
| ≥1.0 mg/L | 2.4 | 2.62 (1.31 to 5.23) | |
| Cerebral stroke | | | |
| <1.0 mg/L | 2.3 | 0.98 (0.77 to 1.24) | 0.17 |
| ≥1.0 mg/L | 3.8 | 1.37 (0.89 to 2.12) | |

(1) Cardiovascular Disease

The 5 year incidence rate was 3.5% in the group with a blood hs-CRP value of less than 1.0 mg/L, while it was higher at 5.9% in the group with a blood hs-CRP value of at least 1.0 mg/L.

The hazard ratio was 0.94 (95% confidence interval; 0.78 to 1.14) in the group with a blood hs-CRP value of less than 1.0 mg/L, and 1.66 (95% confidence interval; 1.14 to 2.42) in the group with a blood hs-CRP value of at least 1.0 mg/L, thus confirming the significant association between the blood hs-CRP value and the hazard ratio (p value=0.01).

In the group with a blood hs-CRP value of at least 1.0 mg/L, it was demonstrated that the risk of the onset of cardiovascular disease significantly increases by 1.66-fold with every decrease in the serum EPA/AA ratio of 0.25.

(2) Coronary Artery Disease

The 5 year incidence rate was 1.3% in the group with a blood hs-CRP value of less than 1.0 mg/L, and higher at 2.4% in the group with a blood hs-CRP value of at least 1.0 mg/L.

The hazard ratio was 0.93 (95% confidence interval; 0.69 to 1.25) in the group with a blood hs-CRP value of less than 1.0 mg/L, and 2.62 (95% confidence interval; 1.31 to 5.23) in the group with a blood hs-CRP value of at least 1.0 mg/L, thus confirming the significant association between the blood hs-CRP value and the hazard ratio was recognized (p value=0.008).

In the group with a blood hs-CRP value of at least 1.0 mg/L, it was demonstrated that the risk of the onset of coronary artery disease significantly increases by 2.62-fold with every decrease in the serum EPA/AA ratio of 0.25.

(3) Cerebral Stroke

The 5 year incidence rate was 2.3% in the group with a blood hs-CRP value of less than 1.0 mg/L, and higher at 3.8% in the group with a blood hs-CRP value of at least 1.0 mg/L.

The hazard ratio was 0.98 (95% confidence interval; 0.77 to 1.24) in the group with a blood hs-CRP value of less than 1.0 mg/L, and 1.37 (95% confidence interval; 0.89 to 2.12) in the group with a blood hs-CRP value of at least 1.0 mg/L. The p value of heterogeneity was 0.17 between the blood hs-CRP value and the hazard ratio.

In the group with a blood hs-CRP value of at least 1.0 mg/L, it was demonstrated that the risk of the onset of cerebral stroke increases by 1.37-fold with every decrease in the serum EPA/AA ratio of 0.25.

7. Relation Between Administration of the Statin Drug and EPA and the Number of Events The group with a blood hs-CRP value of at least 1.0 mg/L (high hs-CRP group) was extracted from the entire subjects. The blood hs-CRP value was quantitated by using a commercially available assay kit.

The high hs-CRP group was further divided into 4 groups by the administration and non-administration of the statin drug and the administration and non-administration of the EPA.

The events of cardiovascular disease, coronary artery disease, and cerebral stroke for each group are shown in Table 4. In the table, "statin (−)+EPA (−)" means that neither the statin drug nor the EPA was administered to a subject; "statin (+)+EPA (−)" means that the statin drug was administered but not the EPA; "statin (−)+EPA (+)" means that the statin drug was not administered despite the administration of the EPA; and "statin (+)+EPA (+)" means that both the statin drug and the EPA were administered. Furthermore, "event (−)" and "event (+)" respectively represent cases with or without events.

Table 4 shows the number of times of occurrence or non-occurrence of events of cardiovascular disease, coronary artery disease, and cerebral stroke and the number of subjects in each group for the high hs-CRP group.

Figure 2:
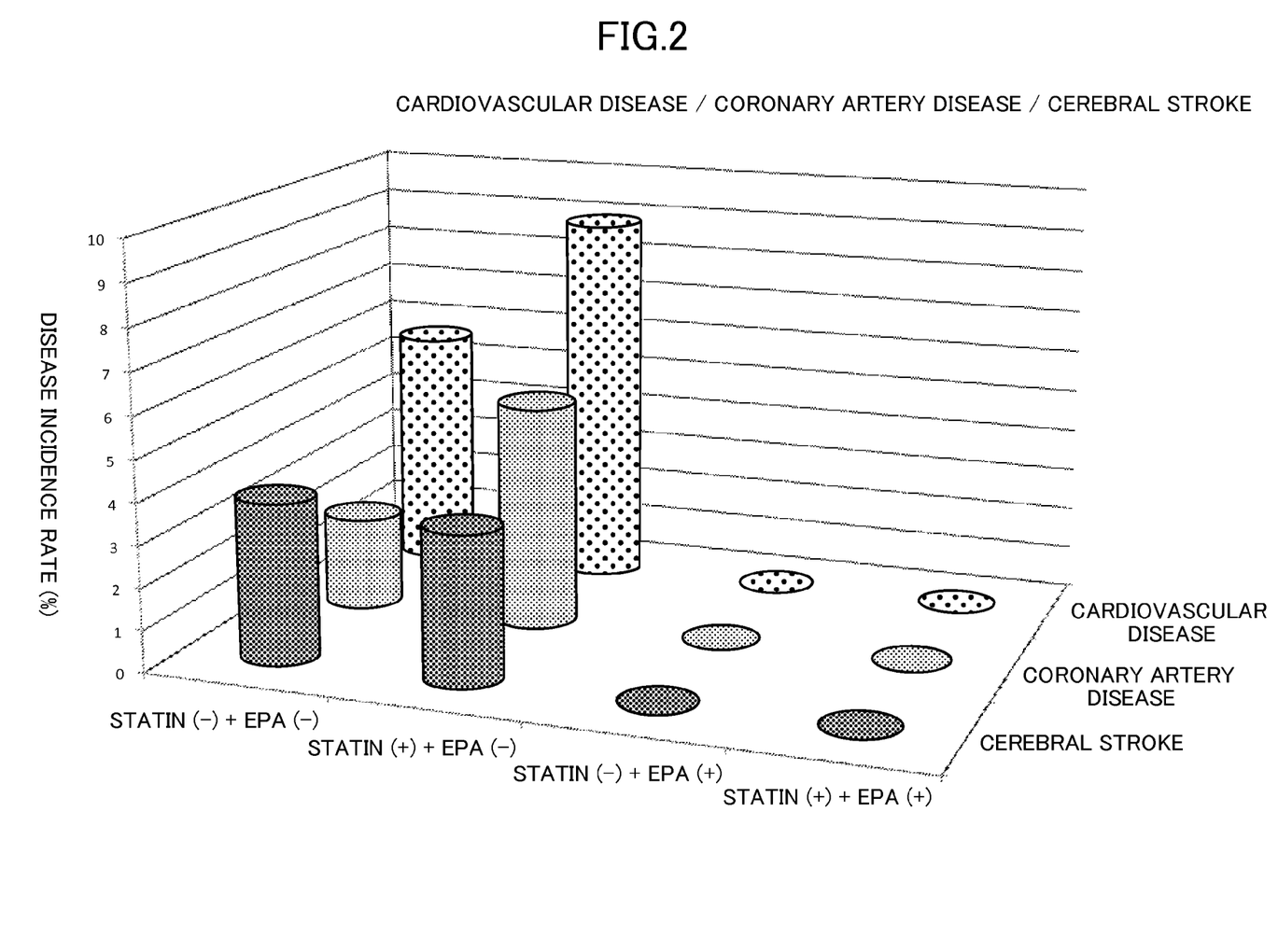
FIG. 2 is a graph showing the relation between the administration and non-administration of the statin drug and the administration and non-administration of the EPA and the disease incidence rate (%) of cardiovascular disease, coronary artery disease, and cerebral stroke for the group with a blood hs-CRP value of at least 1.0 mg/L (high hs-CRP group).

FIG. 2 shows the incidence rate of cardiovascular disease (%), the incidence rate of coronary artery disease (%), and the incidence rate (%) of cerebral stroke for each group.

TABLE 4

| | | | Event (−) | Event (+) | Total |
|---|---|---|---|---|---|
| High hs-CRP group (hs-CRP ≥1.0 mg/L) | Cardiovascular disease | Statin (−) + EPA (−) | 691 | 42 | 733 |
| | | Statin (+) + EPA (−) | 51 | 5 | 56 |
| | | Statin (−) + EPA (+) | 4 | 0 | 4 |
| | | Statin (+) + EPA (+) | 1 | 0 | 1 |
| | Coronary artery disease | Statin (−) + EPA (−) | 717 | 16 | 733 |
| | | Statin (+) + EPA (−) | 53 | 3 | 56 |
| | | Statin (−) + EPA (+) | 4 | 0 | 4 |
| | | Statin (+) + EPA (+) | 1 | 0 | 1 |
| | Cerebral stroke | Statin (−) + EPA (−) | 705 | 28 | 733 |
| | | Statin (+) + EPA (−) | 54 | 2 | 56 |
| | | Statin (−) + EPA (+) | 4 | 0 | 4 |
| | | Statin (+) + EPA (+) | 1 | 0 | 1 |

(1) Cardiovascular Disease

With regard to the cardiovascular disease, no event occurred in the group administered with the EPA in the high hs-CRP group irrespective of the administration of the statin drug.

Furthermore, in the group with no administration of the EPA, the group administered with the statin drug exhibited higher event occurrence compared to the group with no administration of the statin drug, and conceivably, this is because the group administered with the statin drug is a high risk group due to the presence of the dyslipidemia (hyperlipidemia and/or hypercholesterolemia) or due to the more serious dyslipidemia compared to the group with no administration of the statin drug. More specifically, with regard to the cardiovascular disease, no event occurred in the group administered with the EPA in the high hs-CRP group irrespective of the suffering or seriousness of dyslipidemia.

Accordingly, the agent for primary prevention of cardiovascular disease of the present invention is effective for the primary prevention of cardiovascular disease irrespective of the administration of the statin drug and irrespective of the suffering or seriousness of the dyslipidemia.

(2) Coronary Artery Disease

With regard to the coronary artery disease, no event occurred in the group administered with the EPA in the high hs-CRP group irrespective of the administration of the statin drug.

Furthermore, in the group with no administration of the EPA, the group administered with the statin drug exhibited higher event occurrence compared to the group with no administration of the statin drug, and conceivably, this is because the group administered with the statin drug is a high risk group due to the presence of the dyslipidemia (hyperlipidemia and/or hypercholesterolemia) or due to the more serious dyslipidemia compared to the group with no administration of the statin drug. More specifically, with regard to the coronary artery disease, no event occurred in the group administered with the EPA in the high hs-CRP group irrespective of the suffering or seriousness of dyslipidemia.

Accordingly, the agent for primary prevention of cardiovascular disease of the present invention is effective for the primary prevention of the coronary artery disease irrespective of the administration of the statin drug and irrespective of the suffering or seriousness of the dyslipidemia.

(3) Cerebral Stroke

With regard to the cerebral stroke, no event occurred in the group administered with the EPA in both the high hs-CRP group and the entire subjects irrespective of the administration of the statin drug.

Furthermore, for the group with no administration of the EPA, no remarkable difference in the event occurrence was noted between the group administered with the statin drug and the group with no administration of the statin drug.

Accordingly, the agent for primary prevention of cardiovascular disease of the present invention is effective for the primary prevention of the cerebral stroke irrespective of the administration of the statin drug and irrespective of the suffering or seriousness of the dyslipidemia.

The invention claimed is:

1. A combined marker for evaluating risk of cardiovascular disease of a subject who has no history of onset of cardiovascular disease, wherein the marker comprises a blood high sensitivity C reactive protein value (hs-CRP value) and a serum eicosapentaenoic acid/arachidonic acid ratio (EPA/AA ratio),
    wherein the risk of cardiovascular disease is evaluated to be high when the hs-CRP value is at least 1.0 m/L md the EPA/AA ratio is less than 0.25, md the risk of cardiovascular disease is evaluated to be high when the hs-CRP value is at least 1.0 mg/L and the EPA/AA ratio is at least 0.25 and less than 0.50, and
    wherein the cardiovascular disease is coronary artery disease or cerebral stroke.

2. The combined marker according claim 1, wherein the coronary artery disease is myocardial infarction or angina.

3. The combined marker according to claim 1, wherein the cerebral stroke is cerebral infarction or cerebral hemorrhage.

4. A method for extracting a subject with high risk of cardiovascular disease, comprising the steps of:
    administering an agent for primary prevention of cardiovascular disease to a subject with high risk of cardiovascular disease, wherein the subject is extracted by a method comprising the steps of:
    measuring a blood high sensitivity C reactive protein (hs-CRP) value of a subject;
    measuring a serum eicosapentaenoic acid/arachidonic acid (EPA/AA) ratio of the subject; and
    extracting a subject with high risk of cardiovascular disease by combining the hs-CRP value and the EPA/AA ratio;
    wherein the subject having a hs-CRP value of at least 1.0 mg/L and an EPA/AA ratio of less than 0.50 is extracted as said high risk subject of cardiovascular disease; and
    wherein the subject having the hs-CRP value of at least 1.0 mg/L and the EPA/AA ratio of less than 0.25 is extracted as an ultra-high risk subject of cardiovascular disease, and subject having the hs-CRP value of at least 1.0 mg/L and the EPA/AA ratio of at least 0.25 and less than 0.50 is extracted as a high risk subject of cardiovascular disease.

5. The method for extracting a subject with high risk of cardiovascular disease according to claim 4, wherein the subject has no history of cardiovascular disease.

6. A method for treating coronary artery disease or cerebral stroke treatment-comprising the steps of:
    administering an agent for treating cardiovascular disease to a subject with high risk of cardiovascular disease,
    wherein the subject is extracted by a method comprising the steps of: measuring a blood high sensitivity C reactive protein (hs-CRP) value of a subject; measuring a serum eicosapentaenoic acid/arachidonic acid (EPA/AA) ratio of the subject; and
    extracting a subject with high risk of cardiovascular disease by combining the hs-CRP value and the EPA/AA ratio,
    wherein the subject having a hs-CRP value of at least 1.0 mg/L and a EPA/AA ratio of less than 0.25 is extracted as an ultra-high risk subject of coronary artery disease or cerebral stroke treatment, and the subject having a hs-CRP value of at least 1.0 mg/L and a EPA/AA ratio of at least 0.25 and less than 0.50 is extracted as a high risk subject of coronary artery disease or cerebral stroke treatment,
    wherein the agent comprises at least one member selected from the group consisting of eicosapentaenoic acid, its salts, and its esters as an effective component, and
    wherein the subject has no history of cardiovascular disease.

7. The method for extracting a subject with high risk of cardiovascular disease according to claim 4, wherein the agent comprises at least one member selected from the group consisting of eicosapentaenoic acid, its salts, and its esters as an effective component.

8. The method for extracting a subject with high risk of cardiovascular disease according to claim 4, wherein the cardiovascular disease is cerebral stroke.

9. The method for treating of claim 6, wherein the treatment is for coronary artery disease.

10. The method for extracting a subject with high risk of cardiovascular disease according to claim 6, wherein the cardiovascular disease is myocardial infarction or angina.

11. The method for extracting a subject with high risk of cardiovascular disease according to claim 6, wherein the cerebral stroke is cerebral infarction or cerebral hemorrhage.

* * * * *